United States Patent

Stack et al.

(10) Patent No.: US 6,706,736 B2
(45) Date of Patent: Mar. 16, 2004

(54) ANTIDEPRESSANT AZAHETEROCYCLYLMETHYL DERIVATIVES OF OXAHETEROCYCLE-FUSED-[1,4]-BENZODIOXANS

(75) Inventors: Gary P. Stack, Ambler, PA (US); Hong Gao, Belle Mead, NJ (US); Elizabeth S. Gildersleeve, San Diego, CA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/377,901

(22) Filed: Mar. 3, 2003

(65) Prior Publication Data

US 2003/0162805 A1 Aug. 28, 2003

Related U.S. Application Data

(63) Continuation-in-part of application No. 10/131,340, filed on Apr. 24, 2002, now Pat. No. 6,552,049.
(60) Provisional application No. 60/286,569, filed on Apr. 26, 2001.

(51) Int. Cl.[7] ............................................. A61K 31/4439
(52) U.S. Cl. .................... 514/338; 514/321; 514/300
(58) Field of Search ................. 514/338, 321, 514/300

(56) References Cited

U.S. PATENT DOCUMENTS

| 5,318,988 A | 6/1994 | Schohe-Loop et al. |
| 5,371,094 A | 12/1994 | Heine et al. |
| 5,741,789 A | 4/1998 | Hibschman et al. |
| 5,824,682 A | 10/1998 | Van Lommen et al. |
| 5,869,490 A | 2/1999 | Stack |
| 6,552,049 B2 * | 4/2003 | Stack et al. .................. 514/338 |

FOREIGN PATENT DOCUMENTS

| EP | 0 897 921 | 2/1999 |
| WO | WO 97/23485 | 7/1997 |
| WO | WO 98/16530 | 4/1998 |

* cited by examiner

*Primary Examiner*—Jane Fan
(74) *Attorney, Agent, or Firm*—Woodcock Washburn LLP

(57) ABSTRACT

Compounds of the formula

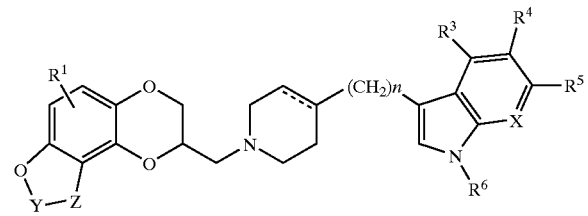

useful for the treatment of depression such as obsessive compulsive disorder, panic attacks, generalized anxiety disorder, social anxiety disorder, sexual dysfunction, eating disorders, obesity, addictive disorders caused by ethanol or cocaine abuse and related illnesses.

2 Claims, No Drawings

ANTIDEPRESSANT AZAHETEROCYCLYLMETHYL DERIVATIVES OF OXAHETEROCYCLE-FUSED-[1,4]-BENZODIOXANS

This application is a continuation-in-part application of 10/131,340, filed on Apr. 24, 2002, now U.S. Pat. No. 6,552,049, which claims the benefit of provisional application Ser. No. 60/286,569, filed on Apr. 26, 2001, the entire disclosure of which is hereby incorporated by reference.

BACKGROUND OF THE INVENTION

Major depression is a serious health problem affecting more than 5% of the population, with a life-time prevalence of 15–20%.

Selective serotonin reuptake inhibitors have produced significant success in treating depression and related illnesses and have become among the most prescribed drugs. They nonetheless have a slow onset of action, often taking several weeks to produce their full therapeutic effect. Furthermore, they are effective in fewer than two-thirds of patients.

Serotonin selective reuptake inhibitors (SSRIs) are well known for the treatment of depression and other conditions. SSRIs work by blocking the neuronal reuptake of serotonin, thereby increasing the concentration of serotonin in the synaptic space, and thus increasing the activation of postsynaptic serotonin receptors.

However, although a single dose of an SSRI can inhibit the neuronal serotonin transporter which would be expected to increase synaptic serotonin, long-term treatment is required before clinical improvement is achieved.

It has been suggested that the SSRIs increase the serotonin levels in the vicinity of the serotonergic cell bodies and that the excess serotonin activates somatodendritic autoreceptors, $5HT_{1A}$ receptors, causing a decrease in serotonin release in major forebrain areas. This negative feedback limits the increment of synaptic serotonin that can be induced by antidepressants.

A $5HT_{1A}$ antagonist would limit the negative feedback and should improve the efficacy of the serotonin reuptake mechanism. (Perez, V., et al., The Lancet, 349:1594–1597 (1997)). Such a combination therapy would be expected to speed up the effect of the serotonin reuptake inhibitor.

Thus, it is highly desirable to provide improved compounds which both inhibit serotonin reuptake and which are antagonists of the $5HT_{1A}$ receptor.

DESCRIPTION OF THE INVENTION

In accordance with this invention, there is provided a group of novel compounds of the formula:

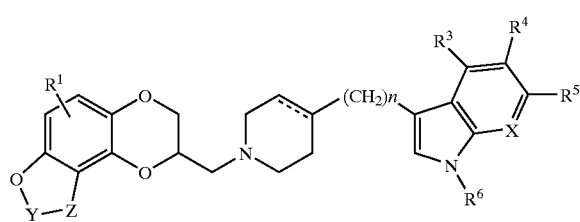

I wherein
$R^1$, $R^3$, $R^4$, $R^5$ and $R^7$ are, independently, hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

Y is C=O or $C(R^2)_2$ and Z is $CH_2$, $CH_2CH_2$, CH=CH or $NR^2$, or Y and Z, taken together, form $CR^2$=CH, N=$CR^2$ or $CR^2$=N;

$R^2$ and $R^6$ are hydrogen or alkyl of 1 to 6 carbon atoms;

X is $CR^7$ or N;

A dotted line represents an optional double bond; and n is an integer 0, 1 or 2;

or a pharmaceutically acceptable salt thereof.

In some preferred embodiments of the present invention $R^1$ is hydrogen, hydroxy, halogen, cyano, trifluoromethyl, alkyl of one to six carbon atoms or alkoxy of one to six carbon atoms. In still more preferred embodiments of the present invention $R^1$ is hydrogen, halo or methoxy.

In other preferred embodiments of the present invention $R^2$ is hydrogen or lower alkyl. Still more preferred are compounds of Formula I wherein $R^2$ is hydrogen.

$R^3$, $R^4$ and $R^5$ is are independently selected from hydrogen, hydroxy, halo, cyano, carboxamido, alkyl of one to six carbon atoms, or alkoxy of one to six carbon atoms in some preferred embodiments of the present invention. $R^3$, $R^4$ and $R^5$ are still more preferably selected from hydrogen, halogen or cyano.

$R^6$ is preferably hydrogen or lower alkyl. $R^6$ is still more preferably hydrogen.

Y is preferably $C(R^2)_2$, Z is preferably $CH_2$, $CH_2CH_2$ or CH=CH or in other preferred embodiments Y and Z, taken together, form $CR^2$=CH.

X is preferably $CR^7$. When X is $CR^7$, $R^7$ is preferably hydrogen, hydroxy, halo, cyano, carboxamido, alkyl of one to six carbon atoms, or alkoxy of one to six carbon atoms. Still more preferably $R^7$ is hydrogen, halogen or cyano.

Still more preferred embodiments of the present invention are those in which $R^1$ is hydrogen, hydroxy, halo, cyano, trifluoromethyl, alkyl of one to six carbon atoms or alkoxy of one to six carbon atoms; Y is C=O or $C(R^2)_2$ and Z is $CH_2$, $CH_2CH_2$ or CH=CH or Y and Z, taken together, form $CR^2$=CH; $R^2$ is hydrogen, or lower alkyl; $R^3$, $R^4$ and $R^5$ are independently selected from hydrogen, hydroxy, halo, cyano, carboxamido, alkyl of one to six carbon atoms, or alkoxy of one to six carbon atoms; n is an integer 0 or 1; and $R^6$ and the dotted line are defined as above.

Most preferred are those examples in which $R^1$ is hydrogen, halo or methoxy, Y is $C(R^2)_2$ and Z is $CH_2$, $CH_2CH_2$ or CH=CH or Y and Z, taken together, form $CR^2$=CH; $R^2$ is hydrogen; $R^3$, $R^4$ and $R^5$ are independently selected from is hydrogen, halo or cyano, $R^6$ is hydrogen, n is 0 and the dotted line in the azaheterocycle represents a double bond.

This invention relates to both the R and S stereoisomers of the aminomethyl-oxaheterocycle-fused-[1,4]-benzodioxan, as well as to mixtures of the R and S stereoisomers. Throughout this application, the name of the product of this invention, where the absolute configuration of the aminomethyl-oxaheterocycle-fused-[1,4]-benzodioxan is not indicated, is intended to embrace the individual R and S enantiomers as well as mixtures of the two. In some preferred embodiments of the present invention the S stereoisomer is preferred.

Where a stereoisomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. Substantially free as used herein means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, IN 1972).

It is further recognized that tautomers of the claimed compounds may exist. The present invention thus encompasses tautomeric forms of compounds of the present invention.

Alkyl as used herein refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

Alkanamido as used herein refers to the group R—C(=O)—NH— where R is an alkyl group of 1 to 5 carbon atoms.

Alkanoyloxy as used herein refers to the group R—C(=O)—O— where R is an alkyl group of 1 to 5 carbon atoms.

Alkanesulfonamido as used herein refers to the group R—S(O)$_2$—NH— where R is an alkyl group of 1 to 6 carbon atoms.

Alkoxy as used herein refers to the group R—O— where R is an alkyl group of 1 to 6 carbon atoms.

Carboxamido as used herein refers to the group —CO—NH$_2$.

Carboalkoxy as used herein refers to the group R—O—C(=O)— where R is an alkyl group of 1 to 5 carbon atoms.

Halogen (or halo) as used herein refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific compounds of the present invention are:
  3-(1-{[8-methyl-2,3-dihydrofuro[2,3-f][1,4]benzodioxin-2-yl]methyl}-1,2,3,6-tetrahydro-4-pyridinyl)-1H-indole;
  3-{1-[2,3,8,9-tetrahydrofuro[3,2-f][1,4benzodioxin-2-ylmethyl]-1,2,3,6-tetrahydro-4-pyridinyl}-1H-indole;
  3-{1-[2,3-dihydrofuro[3,2-f][1,4]benzodioxin-2-ylmethyl]-1,2,3,6-tetrahydro-pyridin-4-yl}-1H-indole;
  3-{1-[2,3,9,10-tetrahydro-8H-[1,4]dioxino[2,3-f]chromen-2-ylmethyl]-1,2,3,6-tetrahydro-4-pyridinyl}-1H-indole; and
  5-fluoro-3-{1-[2,3,9,10-tetrahydro-8H-[1,4]dioxino[2,3-f]chromen-2-ylmethyl]-1,2,3,6-tetrahydro-4-pyridinyl}-1H-indole, and pharmaceutical salts thereof.

The 2-azaheterocyclylmethyl-furo[3,2-f][1,4]benzodioxans of this invention are prepared as illustrated below. Unless otherwise noted, the variables are as defined above. Specifically, the appropriately substituted 4-benzyloxysalicylaldehyde is alkylated with allyl bromide or chloride in the presence of a suitable base such as sodium hydride or potassium carbonate. The aldehyde moiety is then converted to a phenol via oxidation with meta-chloroperoxybenzoic acid (Baeyer-Villiger reaction), followed by cleavage of the resulting formate ester with methanol over basic alumina. The phenol thus obtained is then elaborated via alkylation with a glycidyl halide or tosylate in the presence of a base such as sodium hydride or potassium carbonate and the product submitted to a Claisen rearrangement in a refluxing high-boiling solvent such as mesitylene. Cyclization of the Claisen rearrangement product to the benzodioxan is effected via treatment with methanol and sodium bicarbonate. After conversion of the benzodioxan-2-methanol to the tosylate with p-toluenesulfonyl chloride, diisopropylethylamine and catalytic dimethylaminopyridine, or to a halide via treatment with triphenylphosphine and carbon tetrabromide or chloride, the allyl side chain is cleaved to an aldehyde with sodium periodate and catalytic osmium tetroxide. Following reduction of the aldehyde to the alcohol with a suitable reducing agent such as tetra-n-butylammonium borohydride and removal of the benzyl protecting group with hydrogen over palladium on carbon, cyclization to the dihydrofuran is effected via a Mitsonobu reaction with triphenylphosphine and diethyl or diisopropylazodicarboxylate.

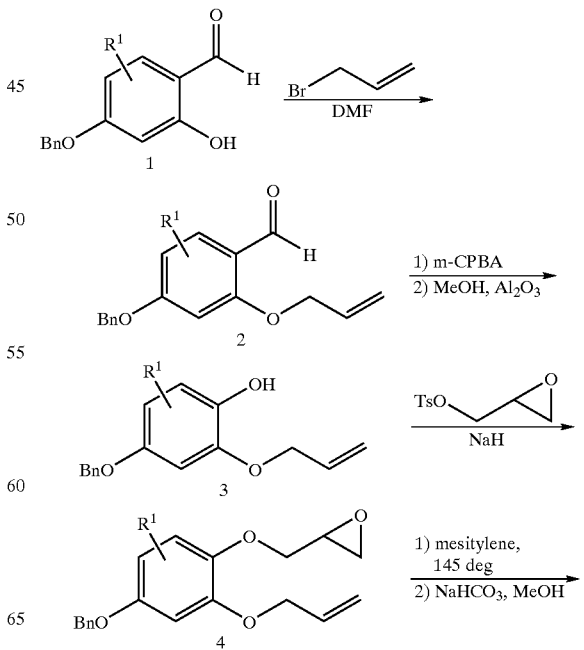

Scheme I

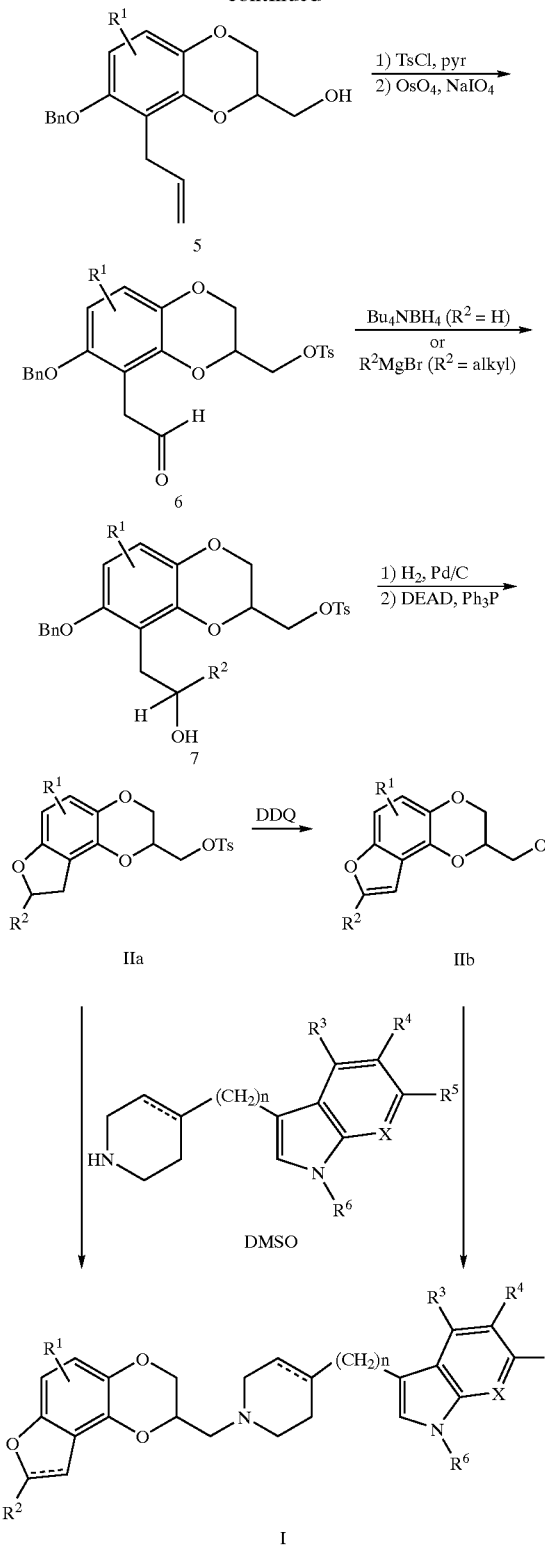

followed by replacement of the halide or tosylate with the appropriate azaheterocycle gives the title compounds of the invention in which the fused heterocycle is furan. Reaction of the aldehyde mentioned above with an appropriate Grignard reagent ($R^2MgBr$) gives the corresponding secondary alcohol, which after deprotection and cyclization as described above leads to compounds of the invention in which $R^2$ is alkyl. Oxidation of the aldehyde mentioned above to the carboxylic acid, using an appropriate oxidant such as Jones' reagent ($CrO_3/H_2SO_4$), followed by deprotection as above and cyclization in acid leads to compounds of the invention in which Y is C=O. Esterification of the carboxylic acid and treatment of the ester with excess Grignard reagent gives a tertiary alcohol, which upon deprotection as above and cyclization in acid leads to compounds of the invention in which the fused dihydrofuran is dialkylated.

The fused furan of the invention in which R is methyl is alternatively prepared by the procedure outlined below in which the appropriately substituted 7-hydroxybenzodioxan-2-methanol is alkylated with 2,3-dichloro-1-propene in the presence of a suitable base such as sodium hydride and the Claisen rearrangement effected by refluxing in a high boiling solvent such as diethylaniline. The regioisomers thus obtained are separated by column chromatography on silica gel and Scheme II

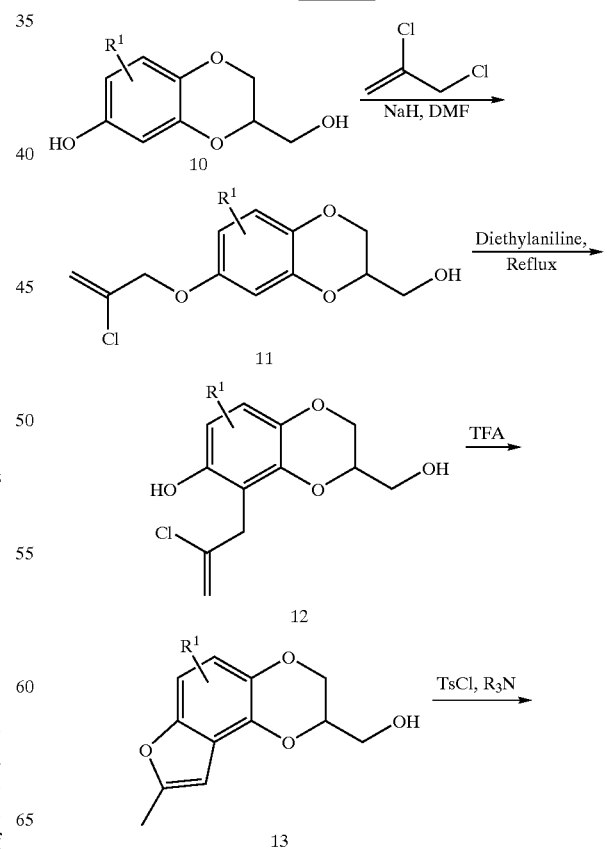

Replacement of the halide or tosylate with the azaheterocyles appropriate to the invention via heating in a high boiling solvent such as dimethyl sulfoxide gives the title compounds of the invention in which the fused heterocycle is dihydrofuran. Alternatively, oxidation of the product of the Mitsonobu cyclization with an oxidant such as DDQ,

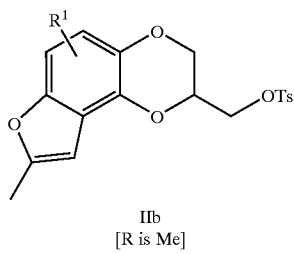

IIb
[R is Me]

the desired 8-(2-chloro-3-propene) derivative cyclized to the furan by treament with trifluoroacetic acid. Tosylation and replacement of the tosyl with the azaheterocycles appropriate to the invention gives the title compounds.

The fused pyrans of this invention are prepared as illustrated below. The 7-benzyloxy-8-allyl benzodioxan-2-methyltosylate described above is treated with borane in tetrahydrofuran, followed by oxidation with hydrogen peroxide to yield the 3-hydroxypropyl derivative. Deprotection of the phenol with hydrogen over palladium on carbon and cyclization with triphenylphosphine and diethyl or diisopropyl azodicarboxylate gives the unsubstituted pyran. Alternatively, oxidation of the alcohol with Jones' reagent or any other suitable oxidant yields the carboxylic acid, which following deprotection as above is cyclized to the lactone by treatment with the appropriate acid. Esterification of the carboxylic acid and treatment of the ester with excess Grignard reagent gives the tertiary alcohol, which following deprotection as above and cyclization in acid gives the disubstituted pyran. As before, replacement of the tosylate with azaheterocycles appropriate to the invention gives the title compounds of the invention.

Unsaturated pyrans (chromenes) are prepared by the method outlined below. Specifically, the appropriately substituted 7-hydroxybenzodioxan-2-methyltosylate is alkylated with a suitable disubstituted propargyl halide (for example, 3-chloro-3-methyl-1-butyne) under the influence of a base such as potassium carbonate or with a disubstituted propargyl alcohol under the Mitsonobu conditions. The resulting ether is rearranged by refluxing in a high boiling solvent such as diethylaniline to give the chromene directly as a mixture of positional isomers. Separation of the regioisomers by column chromatography and replacement of the Scheme III

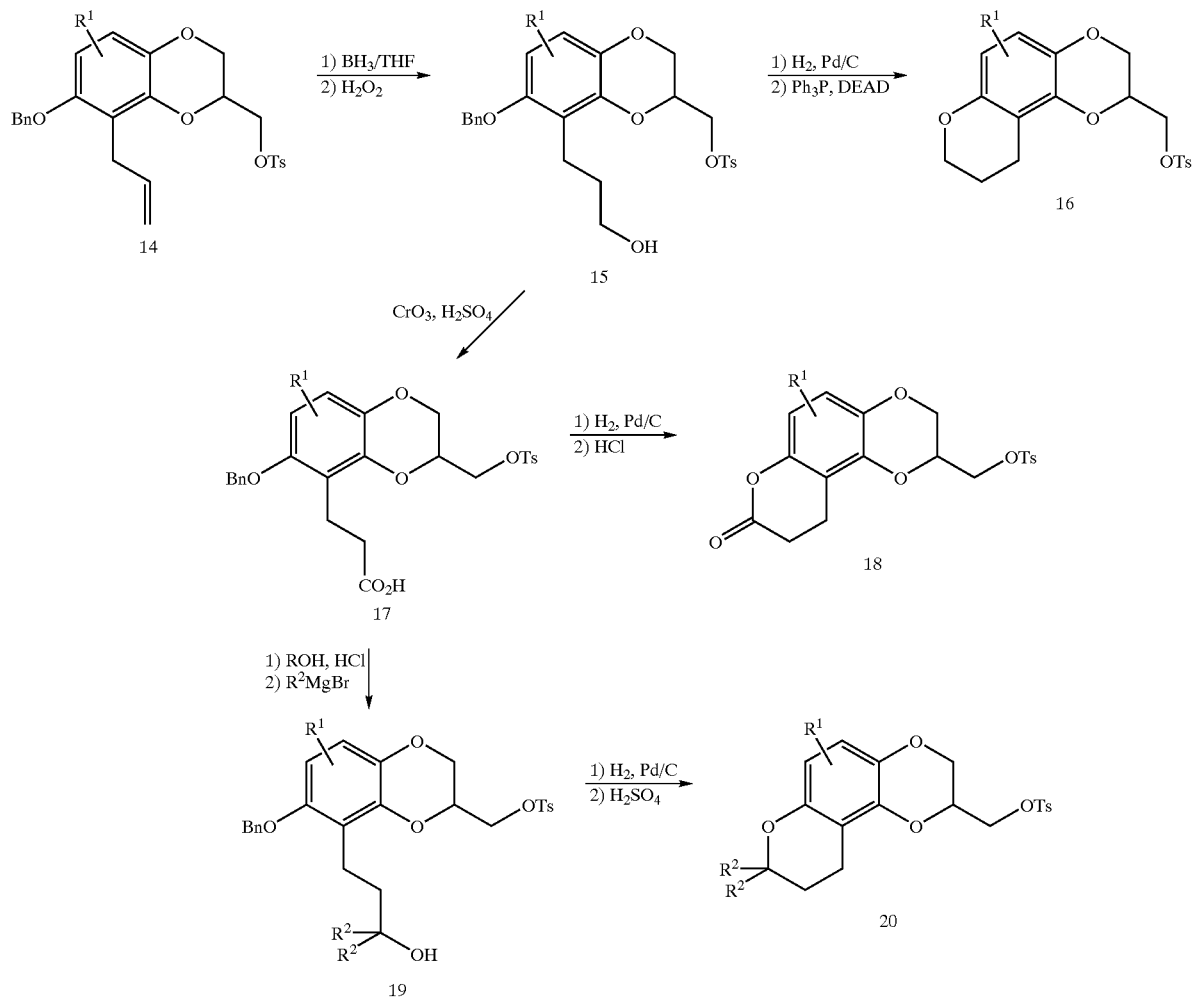

tosylate with the appropriate azaheterocycles gives the title compounds of the invention.

Scheme IV

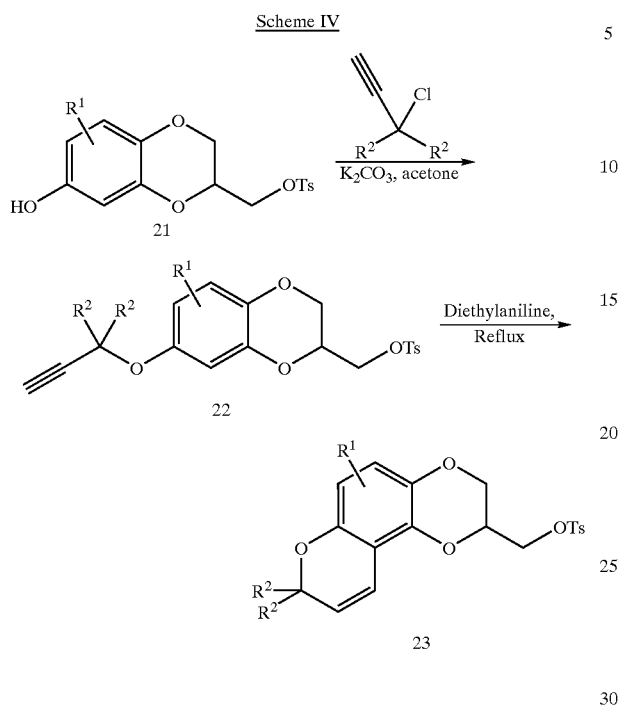

The compounds of the invention in which the fused heterocycle is isoxazole are prepared as illustrated below. The 7-benzyloxy-8-allylbenzodioxan-2-methyltosylate described above is treated with bis(acetonitrile) palladium (II) chloride in refluxing methylene chloride or benzene in order to effect an isomerization of the double bond into conjugation with the aromatic ring. Cleavage of the olefin with osmium tetroxide and sodium periodate then gives the o-benzyloxybenzaldehyde, which is deprotected as above by treatment with hydrogen over palladium on carbon. Cyclization to the isoxazole is effected by treatment with hydroxylamine-O-sulfonic acid and sodium bicarbonate. Alternatively, the aldehyde may be treated with the appropriate Grignard reagent and the resulting secondary alcohol oxidized to a ketone with a suitable oxidant such as pyridinium chlorochromate or the Swern reagent. Deprotection as above and cyclization with hydroxylamine-O-sulfonic acid gives the alkyl substituted isoxazole. As before, replacement of the tosylate with azaheterocycles appropriate to the invention gives the title compounds of the invention.

Scheme V

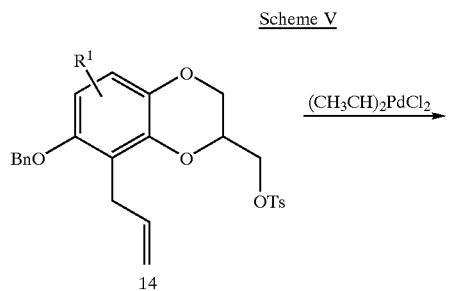

The compounds of the invention in which the fused heterocycle is oxazole are prepared as illustrated below. The o-benzyloxybenzaldehyde described above is treated with a suitable oxidant such as the Jones' reagent ($CrO_3/H_2SO_4$) to give the corresponding carboxylic acid. Treatment of the acid with diphenylphosphoryl azide and a tertiary base such as diisopropylethylamine in t-butanol effects a Curtius reaction and gives the corresponding aniline protected as the t-butoxycarbonyl (t-BOC) derivative. The t-BOC group is removed in an acid such as trifluoroacetic acid and cyclization to the oxazole is effected by refluxing in the appropriate ortho ester. As before, replacement of the tosylate with azaheterocycles appropriate to the invention gives the title compounds of the invention.

Scheme VI

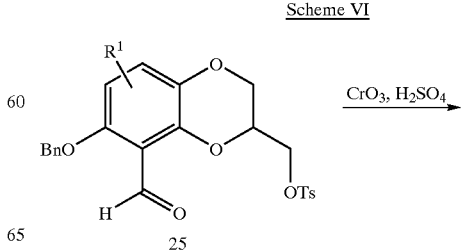

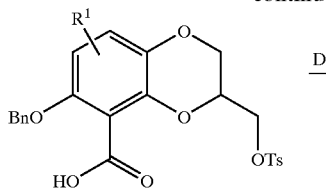

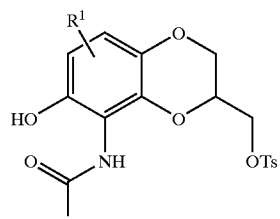

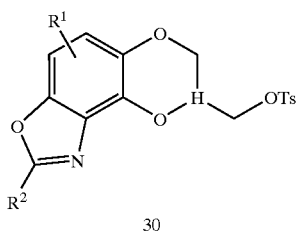

The salicylaldehydes, benzodioxans and azaheterocycles appropriate to the above chemistry are known compounds or can be prepared by one schooled in the art. The compounds of the invention may be resolved into their enantiomers by conventional methods or, preferably, the individual enantiomers may be prepared directly by substitution of (2R)-(−)-glycidyl 3-nitrobenzenesulfonate or tosylate (for the S benzodioxan methanamine) or (2S)-(+)-glycidyl 3-nitrobenzenesulfonate or tosylate (for the R enantiomer) in place of epihalohydrin or racemic glycidyl tosylate in the procedures above.

Like the antidepressants fluoxetine, paroxetine and sertraline, the compounds of this invention have the ability to block the reuptake of the brain neurotransmitter serotonin. They are thus useful for the treatment of depression and other diseases commonly treated by the administration of serotonin selective reuptake inhibitor (SSRI) antidepressants, such as obsessive compulsive disorder, panic attacks, generalized anxiety disorder, social anxiety disorder, sexual dysfunction, eating disorders, obesity, addictive disorders caused by ethanol or cocaine abuse and related illnesses. Moreover, the compounds of this invention have affinity for and antagonist activity at brain 5-HT$_{1A}$ serotonin receptors. Recent clinical trials employing drug mixtures (eg, fluoxetine and pindolol) have demonstrated a more rapid onset of antidepressant efficacy for a treatment combining SSRI activity and 5-HT$_{1A}$ antagonism (Blier and Bergeron, 1995; F. Artigas et. al., 1996; M. B. Tome et. al., 1997). The compounds of the invention are thus exceedingly interesting and useful for treating depressive illnesses.

A protocol similar to that used by Cheetham et. al. (Neuropharmacol. 32:737, 1993) was used to determine the affinity of the compounds of the invention for the serotonin transporter. The compound's ability to displace $^3$H-paroxetine from male rat frontal cortical membranes was determined using a Tom Tech filtration device to separate bound from free $^3$H-paroxetine and a Wallac 1205 Beta Plate® counter to quantitate bound radioactivity. K$_i$'s thus determined for standard clinical antidepressants are 1.96 nM for fluoxetine, 14.2 nM for imipramine and 67.6 nM for zimelidine. A strong correlation has been found between $^3$H-paroxetine binding in rat frontal cortex and $^3$H-serotonin uptake inhibition.

High affinity for the serotonin 5-HT$_{1A}$ receptor was established by testing the claimed compound's ability to displace [$^3$H] 8-OHDPAT (dipropylaminotetralin) from the 5-HT$_{1A}$ serotonin receptor following a modification of the procedure of Hall et al., J. Neurochem. 44, 1685 (1985) which utilizes CHO cells stably transfected with human 5-HT$_{1A}$ receptors. The 5-HT$_{1A}$ affinities for the compounds of the invention are reported below as K$_i$'s.

Antagonist activity at 5-HT$_{1A}$ receptors was established by using a $^{35}$S-GTPγS binding assay similar to that used by Lazareno and Birdsall (Br. J. Pharmacol. 109: 1120, 1993), in which the test compound's ability to affect the binding of $^{35}$S-GTPγS to membranes containing cloned human 5-HT$_{1A}$ receptors was determined. Agonists produce an increase in binding whereas antagonists produce no increase but rather reverse the effects of the standard agonist 8-OHDPAT. The test compound's maximum inhibitory effect is represented as the I$_{max}$, while its potency is defined by the IC$_{50}$.

The results of the three standard experimental test procedures described in the preceding three paragraphs were as follows:

| Compound | 5-HT Transporter Affinity KI (nM) | 5-HT$_{1A}$ Receptor Affinity KI (nM) | 5-HT$_{1A}$ Function IC$_{50}$ (nM) (I$_{max}$) |
|---|---|---|---|
| Example 1 | 185.0 | 14.07 | 241.0 (62.0) |
| Example 2 | 34.0 | 45.96 | 264.0 (66.0) |
| Example 3 | 115.0 | 19.56 | 19.0 (61.0) |
| Example 4 | 8.5 | 30.44 | 868.0 (100) |
| Example 5 | 10.0 | 29.37 | 347.0 (100) |

Hence the compounds of the present invention are combined serotonin reuptake inhibitors/5-HT$_{1A}$ antagonists and are useful for the treatment of diseases commonly treated by the administration of serotonin selective reuptake inhibitor (SSRI) antidepressants, such as depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorder (including trichotillomania), social anxiety disorder, generalized anxiety disorder, obesity, eating disorders such as anorexia nervosa, bulimia nervosa, vasomotor flushing, cocaine and alcohol addiction, sexual dysfunction (including premature ejaculation), and related illnesses.

Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in *Remingtons Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 5 mg per day with gradual increase in the daily dose to about 150 mg per day, to provide the desired dosage level in the human.

Provide as used herein means either directly administering a compound or composition of the present invention, or administering a prodrug, derivative or analog which will form an equivalent amount of the active compound or substance within the body.

The present invention includes prodrugs of compounds of Formula I. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Deliver Reviews, 8:1–38(1992), Bundgaard, J. of Pharmaceutical Sciences, 77:285 et seq. (1988); and Higuchi and Stella (eds.) Prodrugs as Novel Drug Delivery Systems, American Chemical Society (1975).

The following examples illustrate the production of representative compounds of this invention.

INTERMEDIATE 1

{7-][(2-Chloro-2-propenyl)oxy]-2,3-dihydro-1,4-benzodioxin-2-yl}methanol

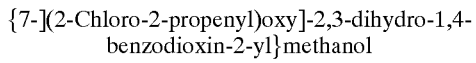

To a solution of 1.36 g (7.47 mmole) of (2S)-(7-hydroxy-2,3-dihydro-1,4-benzodioxin-2-yl)methanol in 50 mL of N,N-dimethylformamide was added 0.36 g (9.0 mmole) of 60% sodium hydride/mineral oil dispersion and the mixture stirred for 30 minutes at room temperature under nitrogen. Next 1.0 mL (11 mmole) of 2,3-dichloro-1-propene was added and the reaction heated at 60° C. under nitrogen for 40 hours. The solvent was removed in vacuum and replaced with 200 mL of methylene chloride. The solution was washed with 50 mL of 0.1 N aqueous HCl and with water, dried over sodium sulfate, filtered and concentrated in vacuum to ~2 g of a very dark oil. The oil was column chromatographed on silica gel with 20% hexane/methylene chloride and the product fractions combined and concentrated in vacuum to give 1.1 g of the (S)-enantiomer of the title compound as a pale yellow oil. $^1$H-NMR (d$_6$-DMSO): doublet 7.76 δ (1H); doublet 6.53 δ (1H); doublet of doublets 6.45 δ (1H); doublet 5.66 δ (1H); doublet 5.48 δ (1H); broad singlet 5.04 δ (1H); singlet 4.6 δ (2H); doublet of doublets 4.25 δ (1H); multiplet 4.12 δ (1H); doublet of doublets 3.92 δ (1H); multiplet 3.6 δ (2H).

INTERMEDIATE 2

5-(2-Chloro-2-propenyl)-3-(hydroxymethyl)-2,3-dihydro-1,4-benzodioxin-6-ol

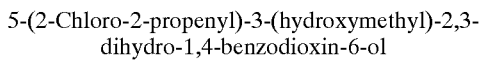

A solution of 1.1 g (4.3 mmole) of {(2S)-7-[(2-chloro-2-propenyl)oxy]-2,3-dihydro-1,4-benzodioxin-2-yl}methanol in 60 mL of N,N-diethylaniline was refluxed under nitrogen for 15 hours. Upon cooling, the mixture was diluted with 250 mL of ethyl acetate and extracted eight times with 50 mL portions of 2 N aqueous HCl. It was then washed with 40 mL of saturated aqueous sodium bicarbonate and with 50 mL of saturated brine, dried over sodium sulfate, filtered and evaporated in vacuum to give 1.4 g of a black oil. This was column chromatographed on silica gel with 0.5% methanol in methylene chloride to give 0.40 g of the (S)-enantiomer of the title compound, as well as 0.39 g of 6-substituted Claisen product, both as pale yellow oils. $^1$H-NMR ($d_6$-DMSO): singlet 9.05 δ (1H); doublet 6.60 δ (1H); doublet 6.30 δ (1H); doublet 5.10 δ (1H); multiplet 5.00 δ (2H); doublet 4.85 δ (1H); doublet of doublets 4.15 δ (1H); multiplet 4.08 δ (1H); doublet of doublets 3.90 δ (1H); multiplet 3.55 δ (2H); singlet 3.50 δ (2H).

INTERMEDIATE 3

[8-Methyl-2,3-dihydrofuro[3,2-f][1,4]benzodioxin-2-yl]methanol

A solution of 0.40 g (1.6 mmole) of (3S)-5-(2-chloro-2-propenyl)-3-(hydroxymethyl)-2,3-dihydro-1,4-benzodioxin-6-ol in 70 mL of trifluoroacetic acid was stirred at room temperature for 26 hours. The solvent was then removed in vacuum and replaced with 100 mL of methanol. Potassium carbonate (3.0 g, 2.2 mmole) was added and the mixture stirred for an additional 1.5 hours at room temperature. The mixture was then filtered and the filtrate concentrated to a brown residue in vacuum. The residue was column chromatographed on silica gel with methylene chloride as eluant to give 0.20 g (60%) of the (S)-enantiomer of the title compound as a yellow oil. $^1$H-NMR ($d_6$-DMSO): doublet 6.94 δ (1H); doublet 6.71 δ (1H); singlet 6.48 δ (1H); triplet 5.07 δ (1H); doublet of doublets 4.30 δ (1H); multiplet 4.22 δ (1H); multiplet 4.00 δ (1H); multiplet 3.65 δ (2H); singlet 2.38 δ (3H).

INTERMEDIATE 4

[8-Methyl-2,3-dihydrofuro[3,2-f][1,4]benzodioxin-2-yl]methyl 4-Methylbenzenesulfonate To a solution of 0.20 g (0.90 mmole) of [(2S)-8-methyl-2,3-dihydrofuro[3,2-f][1,4]benzodioxin-2-yl]methanol in 5.0 mL of pyridine was added 1.0 g (5.2 mmole) of p-toluenesulfonyl chloride. The mixture was stirred at room temperature under nitrogen for 15 hours. The solvent was then removed in vacuum and replaced with 200 mL of methylene chloride. The solution was washed with 100 mL portions of 2 N aqueous HCl, saturated aqueous sodium bicarbonate and saturated brine, dried over magnesium sulfate, filtered and concentrated in vacuum to a brown residue. The residue was column chromatographed on silica gel with 1:1 methylene chloride/hexane as eluant and the product fractions combined and concentrated in vacuum to give 0.28 g of the (R)-enantiomer of the title compound as a pale yellow oil. $^1$H-NMR (CDCl$_3$): doublet 7.79 δ (2H); doublet 7.30 δ (2H); doublet 6.86 δ (1H); doublet 6.68 δ (1H); singlet 6.29 δ (1H); multiplet 4.48 δ (1H); multiplet 4.26 δ (3H); doublet of doublets 4.06 δ (1H); singlet 2.43 δ (3H); singlet 2.41 δ (3H).

EXAMPLE 1

3-(1-{[8-Methyl-2,3-dihydrofuro[2,3-f][1,4]benzodioxin-2-yl]methyl}-1,2,3,6-tetrahydro-4-pyridinyl)-1H-indole To a solution of 0.28 g (0.75 mmole) of [(2R)-8-methyl-2,3-dihydrofuro[3,2-f][1,4]benzodioxin-2-yl]methyl 4-methylbenzenesulfonate and 0.45 g (2.3 mmole) of 3-(1,2,3,6-tetrahydro-4-pyridinyl)-1H-indole in 10 mL of 1:1 tetrahydro-furan/dimethylformamide was added 1.5 g (1.1 mmole) of potassium carbonate and the mixture was refluxed under nitrogen for 15 hours. Upon cooling to room temperature, the reaction mixture was filtered and the filtrate concentrated in vacuum. The residue was column chromatographed on silica gel with 50% hexane/ethyl acetate to give 0.13 g of the (S)-enantiomer of the title compound as a yellow solid, m.p. 198–200° C.

Elemental Analysis for: $C_{25}H_{24}N_2O_3 \cdot 0.60\ H_2O$; Calc'd: C, 73.01; H, 6.18; N, 6.81; Found: C, 73.38; H, 5.97; N, 7.40.

INTERMEDIATE 5

2-Allyloxy4-(benzyloxy)benzaldehyde

A solution of 45.8 g (0.20 mole) 2-hydroxy-4-(benzyloxy) benzaldehyde in 250 mL of dimethylformamide was added dropwise over 1 hour to a slurry of 10.6 g (0.26 mole) of 60% sodium hydride/mineral oil dispersion in 100 mL of dimethylformamide. The mixture was stirred under nitrogen for 1 hour at room temperature, and then 28 mL (0.33 mole) of allyl bromide in 30 mL of dimethylformamide was added. The reaction was heated at 60° C. for 4 hours under nitrogen. The solvent was then removed in vacuum and replaced with 500 mL of ethyl acetate. This solution was washed with 500 mL portions of 2 N aqueous HCl, saturated aqueous sodium bicarbonate and saturated brine, dried over sodium sulfate, filtered and concentrated in vacuum to give 53.6 g (100%) of the title compounds as a pale yellow solid. $^1$H-NMR ($d_6$-DMSO): singlet 10.2 δ (1H); doublet of doublets 7.65 δ (1H); multiplet 7.40 δ (5H); doublet 6.80 δ (1H); doublet of doublets 6.75 δ (1H); multiplet 6.05 δ (1H); doublet of doublets 5.45 δ (1H); doublet of doublets 5.30 δ (1H); singlet 5.20 δ (2H); multiplet 4.70 δ (2H).

INTERMEDIATE 6

2-Allyloxy-4-(benzyloxy)phenol

To a solution of 53.6 g (0.20 mole) of 2-allyloxy-4-(benzyloxy)benzaldehyde in 500 mL of methylene chloride was added a solution of 90 g (~0.3 mole) of 57–86% m-chloroperoxybenzoic acid in 500 mL of methylene chloride. The mixture was stirred at room temperature for 3 days. It was then diluted to 2 L with methylene chloride and washed four times with 500 mL portions of saturated aqueous sodium bicarbonate, dried over magnesium sulfate, filtered and concentrated in vacuum to a brown oil. This was redissolved in 1 L of methanol, 110 g of basic alumina added and the mixture stirred at room temperature for 15 hours. The alumina was removed by filtration and the filtrate concentrated to 50 g of a yellow solid. The crude solid was column chromatographed on silica gel with hexane/methylene chloride as eluant to give 33 g of the title compound as a white solid, m.p. 62° C.

Elemental Analysis for: $C_{16}H_{16}O_3$; Calc'd: C, 74.98; H, 6.29; Found: C, 75.27; H, 6.31.

INTERMEDIATE 7

2-{[2-(Allyloxy)-4-(benzyloxy)phenoxy]methyl]oxirane

Sodium hydride (4.3 g, 0.11 mole of 60% mineral oil dispersion) was washed with hexane and suspended in 100 mL of N,N-dimethylformamide. To this suspension was added a solution of 25.4 g (0.10 mole) of 2-allyloxy-4-(benzyloxy)phenol in 100 mL of DMF. The mixture was stirred at room temperature for 30 minutes and then 22.8 g (0.10 mole) of (2R)-(−)-glycidyl tosylate was added.

The mixture was heated at 60° C. under nitrogen for 2 hours and then at 35° C. for 15 hours. The solvent was removed in vacuum and replaced with 800 mL of methylene chloride. The resulting solution was washed with 200 mL of water and the water back-extracted with 200 mL of methylene chloride. The combined organic phases were washed with 400 mL of saturated brine, dried over sodium sulfate, filtered and concentrated in vacuum to a brown solid. Column chromatography on silica gel with methylene chloride as eluant gave 28.5 g of the (S)-enantiomer of the title compound as a white solid.

Elemental Analysis for: $C_{19}H_{20}O_4$; Calc'd: C, 73.06; H, 6.45; Found: C, 72.67; H, 6.50.

INTERMEDIATE 8

[8-Allyl-7-(benzyloxy)-2,3-dihydro-1,4-benzodioxin-2-yl]methanol

A solution of (2S)-2-{[2-(allyloxy)-4-(benzyloxy)phenoxy]methyl}oxirane (28.5 g, 91.3 mmole) in 1 L of mesitylene was refluxed under nitrogen for 2 days. The solvent was then removed in vacuum and replaced with 500 mL of ethanol. Sodium bicarbonate (25.0 g) was added and the mixture was stirred under nitrogen for 15 hours. The mixture was filtered, the ethanol was removed in vacuum and 500 mL of methylene chloride added. This solution was washed with 500 mL portions of water and saturated brine, dried over sodium sulfate, filtered and concentrated in vacuum to a dark oil. This was column chromatographed on silica gel with methylene chloride as eluant to give 15.6 g of the (S)-enantiomer of the title compound as a tan oil. $^1$H-NMR (CDCl$_3$): multiplet 7.4 δ (5H); doublet 6.7 δ (1H); doublet 6.5 δ (1H); multiplet 6.0 δ (1H); singlet 5.05 δ (2H); multiplet 5.0 δ (2H); multiplet 4.3 δ (2H); doublet of doublets 4.1 δ (1H); doublet of doublets 3.8 δ (2H); multiplet 3.5 δ (2H), broad singlet 1.9 δ (1H).

INTERMEDIATE 9

[8-Allyl-7-(benzyloxy)-2,3-dihydro-1,4-bezodioxin-2-yl]methyl 4-Methylbenzenesulfonate To a solution of 15.6 g (50.0 mmole) of [(2S)-8-allyl-7-(benzyloxy)-2,3-dihydro-1,4-benzodioxin-2-yl]methanol in 100 mL of methylene chloride was added 26.3 mL (0.15 mole) of N,N-diisopropylethylamine, 0.63 g (5 mmole) of 4-dimethyl-aminopyridine and 14.25 g (75.0 mmole) of p-toluenesulfonyl chloride. The mixture was stirred at room temperature under nitrogen for 15 hours. The solvent was then removed in vacuum and the residue column chromatographed on silica gel with methylene chloride as eluant. Combination of the product fractions and concentration in vacuum gave 18.0 g (77%) of the (R)-enantiomer of the title compound as a white solid, m.p. 76–77° C.

Elemental Analysis for: $C_{26}H_{26}O_6S$; Calc'd: C, 66.93; H, 5.62; Found: C, 67.22; H, 5.53.

INTERMEDIATE 10

[7-(Benzyloxy)-8-(2-hydroxyethyl)-2,3-dihydro-1,4-benzodioxin-2-yl]methyl 4-Methylbenzenesulfonate To a solution of 3.9 g (8.4 mmole) of [(2R)-8-allyl-7-(benzyloxy)-2,3-dihydro-1,4-bezodioxin-2-yl]methyl 4-methylbenzenesulfonate in 300 mL of tetrahydrofuran was added 1.8 mL (0.30 mmole) of 4% aqueous osmium tetroxide. The solution was stirred at room temperature under nitrogen for 30 minutes, then a solution of 9.0 g (40 mmole) of sodium periodate in 75 mL of water was added dropwise over a 30 10 minute period. The mixture was allowed to stir at room temperature under nitrogen for 15 hours. Ethyl acetate (400 mL) was then added and the solution was washed twice with 300 mL portions of water and with saturated brine, dried over sodium sulfate, filtered and concentrated in vacuum to 2.8 g of a colorless oil. The oil was redissolved in 100 mL of methylene chloride, 3.0 g (12 mmole) of tetra-n-butylammonium borohydride added and the mixture stirred at room temperature for 15 hours. The excess reducing agent was then destroyed by the cautious addition of 200 mL of 1 N aqueous HCl, the organic phase removed in a separatory funnel, and the aqueous back-extracted with 100 mL of methylene chloride. The combined organic phases were washed with 250 mL of saturated brine, dried over sodium sulfate, filtered and concentrated in vacuum. The residue was column chromatographed on silica gel with first methylene chloride, then 2% methanol in methylene chloride, to give 2.3 g of the (R)-enantiomer of the title compound as a colorless oil. $^1$H-NMR (CDCl$_3$): doublet 7.8 δ (2H); multiplet 7.4 δ (5H); doublet 7.37 δ (2H); doublet 6.65 δ (1H); doublet 6.45 δ (1H); singlet 5.0 δ (2H); multiplet 4.43 δ (1H); multiplet 4.2 δ (3H); doublet of doublets 4.0 δ (1H); triplet 3.73 δ (2H), triplet 2.9 δ (2H); singlet 2.43 δ (3H); broad singlet 1.65 δ (1H).

INTERMEDIATE 11

2,3.8,9-Tetrahydrofuro[3,2-f][1,4]benzodioxin-2-ylmethyl 4-Methylbenzenesulfonate A solution of 2.3 g (4.9 mmole) of [(2R)-7-(benzyloxy)-8-(2-hydroxyethyl)-2,3-dihydro-1,4-benzodioxin-2-yl]methyl 4-methylbenzenesulfonate in 100 mL of methanol was added to a slurry of 0.40 g of 10% palladium on carbon in 30 mL of methanol in 500 mL Parr hydrogenation bottle. The mixture was treated with 50 psi of hydrogen on a Parr shaker for 15 hours. The catalyst was then removed by filtration through celite and the filtrate concentrated in vacuum to 1.72 g of a yellow oil. The oil was dissolved in 100 mL of benzene, 2.1 g (8.0 mmole) of triphenylphosphine and 1.6 g (8.0 mmole) of diisopropylazodicarboxylate added and the mixture stirred at room temperature for 3 days. The solvent was then removed in vacuum and the residue column chromatographed on silica gel with methylene chloride as eluant to give 1.25 g of the (R)-enantiomer of the title compound as a white solid, m.p. 95–96° C.

Elemental Analysis for: $C_{18}H_{18}O_6S$; Calc'd: C, 59.66; H, 5.01; Found: C, 59.78; H, 5.02.

EXAMPLE 2

3-{1-[2,3,8,9-Tetrahydrofuro[3,2-f][1,4]benzodioxin-2-ylmethyl]-1,2,3,6-tetrahydro-4-pyridinyl}-1H-indole A solution of 0.65 g (1.8 mmole) of (2R)-2,3,8,9-tetrahydrofuro[3,2-f][1,4]benzodioxin-2-ylmethyl 4-methylbenzenesulfonate and 1.0 g (5.0 mmole) of 3-(1,2,3,6-tetrahydro-4-pyridinyl)-1H-indole in 10 mL of DMSO was heated under nitrogen at 80° C. for 4 hours. After the reaction had cooled to room temperature, 400 mL of ethyl acetate was added and the solution was washed with 250 mL portions of saturated aqueous sodium bicarbonate, water and saturated brine, dried over sodium sulfate, filtered and concentrated in vacuum. The residue was column chromatographed on silica gel with 2% methanol in chloroform to give 0.32 g of the (S)-enantiomer of the title compound as a gold solid, m.p. 207–209° C.

Elemental Analysis for: $C_{24}H_{24}N_2O_3 \cdot 0.50\ H_2O$; Calc'd: C, 72.52; H, 6.34; N, 7.05; Found: C, 72.87; H, 5.99; N, 7.12.

INTERMEDIATE 12

2,3-Dihydrofuro[3,2-f][1,4]benzodioxin-2-ylmethyl 4-Methylbenzenesulfonate

A solution of 0.54 g (0.67 mmole) of (2R)-2,3,8,9-tetrahydrofuro[3,2-f][1,4]benzodioxin-2-ylmethyl 4-methylbenzenesulfonate and 0.46 g (2.0 mmole) of 2,3-dichloro-5,6-dicyano-1,4-benzoquinone in 20 ml of benzene was refluxed under nitrogen for 15 hours. The solvent was removed in vacuum and the residue column chromatographed on silica gel with methylene chloride as eluant. The product fractions were combined and concentrated in vacuum to give 0.40g of the (R)-enantiomer of the of the title compound as a tan solid. $^1$H-NMR (CDCl$_3$): doublet 7.8 δ (2H); doublet 7.52 δ (1H); doublet 7.3 δ (2H); doublet 6.95 δ (1H); doublet 6.8 δ (1H); doublet 6.65 δ (1H); multiplet 4.5 δ (1H); multiplet 4.25 δ (3H); doublet of doublets 4.1 δ (1H); singlet 2.4 δ (3H).

EXAMPLE 3

3-{1-[2,3-Dihydrofuro[3,2-f][1,4]benzodioxin-2-ylmethyl]-1,2,3,6-tetrahydropyridin-4-yl}-1H-indole A solution of 0.40 g (1.1 mmole) of (2R)-2,3-dihydrofuro[3,2-f][1,4]benzodioxin-2-ylmethyl 4-methylbenzenesulfonate and 1.0 g (5.0 mmole) of 3-(1,2,3,6-tetrahydro-4-pyridinyl)-1H-indole in 10 mL of DMSO was heated under nitrogen at 80° C. for 4 hours. After the reaction had cooled to room temperature, 400 mL of ethyl acetate was added and the solution was washed with 250 mL portions of saturated aqueous sodium bicarbonate, water and saturated brine, dried over sodium sulfate, filtered and concentrated in vacuum. The residue was column chromatographed on silica gel with 2% methanol in chloroform to give 0.27 g of the (S)-enantiomer of the title compound as a white solid, m.p. 208–209° C.

Elemental Analysis for: $C_{24}H_{22}N_2O_3 \cdot 0.25\ H_2O$; Calc'd: C, 73.73; H, 5.80; N, 7.17; Found: C, 73.87; H, 5.57; N, 7.17.

INTERMEDIATE 13

[7-(Benzyloxy)-8-(3-hydroxypropyl)-2,3-dihydro-1,4-benzodioxin-2-yl]methyl 4-Methylbenzenesulfonate To a solution of 4.46 g (9.6 mmole) of [(2R)-8-allyl-7-(benzyloxy)-2,3-dihydro-1,4-bezodioxin-2-yl]methyl 4-methylbenzenesulfonate in 30 mL of tetrahydrofuran at 10° C. was added 21 mL (21 mmole) of 1 M borane/tetrahydrofuran. The solution was allowed to come to room temperature and stir under nitrogen for 3 days. Saturated aqueous sodium bicarbonate (50 mL) was cautiously added, followed by 2.5 mL of 30% hydrogen peroxide. The mixture was stirred at room temperature under nitrogen for 2 hours, then it was extracted with three 60 mL portions of ether. The combined extracts were dried over magnesium sulfate, filtered and concentrated in vacuum to give 4.87 g of the (R)-enantiomer of the title compound as a colorless oil. $^1$H-NMR (CDCl$_3$): doublet 7.8 δ (2H); multiplet 7.4 δ (5H); doublet 7.35 δ (2H); doublet 6.65 δ (1H); doublet 6.45 δ (1H); singlet 5.0 δ (2H); multiplet 4.45 δ (1H); multiplet 4.2 δ (3H); doublet of doublets 4.0 δ (1H); triplet 3.5 δ (2H); doublet of triplets 2.73 δ (2H); singlet 2.45 δ (3H); multiplet 1.75 δ (2H).

INTERMEDIATE 14

2,3,9,10-Tetrahydro-8H-[1,4]dioxino[2,3-f]chromen-2-ylmethyl 4-Methylbenzenesulfonate A solution of 2.0 g (4.1 mmole) of [(2R)-7-(benzyloxy)-8-(3-hydroxypropyl)-2,3-dihydro-1,4-benzodioxin-2-yl] methyl 4-methylbenzenesulfonate in 100 mL of methanol was added to a slurry of 0.30 g of 10% palladium on carbon in 30 mL of methanol in 500 mL Parr hydrogenation bottle. The mixture was treated with 50 psi of hydrogen on a Parr shaker for 15 hours. The catalyst was then removed by filtration through celite and the filtrate concentrated in vacuum to 1.6 g of a colorless oil. The oil was dissolved in 100 mL of benzene, 2.1 g (8.0 mmole) of triphenylphosphine and 1.6 g (8.0 mmole) of diisopropylazodicarboxylate added and the mixture stirred at room temperature for 5 days. The solvent was then removed in vacuum and the residue column chromatographed on silica gel with methylene chloride as eluant to give 1.2 g of the (R)-enantiomer of the title compound as a pale yellow oil. $^1$H-NMR (CDCl$_3$): doublet 7.8 δ (2H); doublet 7.35 δ (2H); doublet 6.6 δ (1H); doublet 6.35 δ (1H); multiplet 4.4 δ (1H); multiplet 4.2 δ (3H); triplet 4.1 (2H); doublet of doublets 4.0 δ (1H); multiplet 2.55 δ (2H); singlet 2.45 δ (3H); multiplet 1.9 δ (2H).

EXAMPLE 4

3-{1-[2,3,9,10-Tetrahydro-8H-[1,4]dioxino[2,3-f]chromen-2-ylmethyl]-1,2,3,6-tetrahydro-4-pyridinyl}-1H-indole A solution of 0.55 g (1.5 mmole) of (2R)-2,3,9,10-tetrahydro-8H-[1,4]-dioxino[2,3-f]chromen-2-ylmethyl 4-methylbenzenesulfonate and 1.0 g (5.0 mmole) of 3-(1,2,3,6-tetrahydro-4-pyridinyl)-1H-indole in 10 mL of DMSO was heated under nitrogen at 80° C. for 4 hours. After the reaction had cooled to room temperature, 400 mL of ethyl acetate was added and the solution was washed with 250 mL portions of saturated aqueous sodium bicarbonate, water and saturated brine, dried over sodium sulfate, filtered and concentrated in vacuum. The residue was column chromatographed on silica gel with 2% methanol in chloroform to give 0.30 g of material which was contaminated by a slightly less polar material. A second column chromatography on silica gel with 0.5% methanol/chloroform gave 0.21 g of the desired product as a pale yellow foam. This was triturated with hot isopropanol to give 0.070 g of the (S)-enantiomer of the title compound as a pale yellow solid, m.p. 186–187° C.

Elemental Analysis for: $C_{25}H_{26}N_2O_3 \cdot 0.15\ H_2O$; Calc'd: C, 74.11; H, 6.54; N, 6.91; Found: C, 74.12; H, 6.54; N, 6.82.

EXAMPLE 5

5-Fluoro-3-{1-[2,3,9,10-tetrahydro-8H-[1,4]dioxino[2,3-f]chromen-2-ylmethyl]-1,2,3,6-tetrahydro-4-pyridinyl}-1H-indole A solution of 0.55 g (1.5 mmole) of (2R)-2,3,9,10-tetrahydro-8H-[1,4]-dioxino[2,3-f]chromen-2-ylmethyl 4-methylbenzenesulfonate and 1.0 g (4.6 mmole) of 5-fluoro-3-(1,2,3,6-tetrahydro-4-pyridinyl)-1H-indole in 10 mL of DMSO was heated under nitrogen at 80° C. for 6 hours. After the reaction had cooled to room temperature, 400 mL of ethyl acetate was added and the solution was washed with 250 mL portions of saturated aqueous sodium bicarbonate, water and saturated brine, dried over sodium sulfate, filtered and concentrated in vacuum. The residue was column chromatographed on silica gel with 0.5% methanol in chloroform to give 0.34 g of the desired product as a pale yellow foam. This was crystallized from ethanol with the addition of 0.10 g of fumaric acid to give 0.24 g of the (S)-enantiomer of the title compound as a pale yellow solid, m.p. 205–206° C.

Elemental Analysis for: $C_{25}H_{25}FN_2O_3 \cdot 0.50\ C_4H_4O_4 \cdot 0.50\ H_2O$; Calc'd: C, 66.52; H, 5.79; N, 5.75; Found: C, 66.58; H, 5.64; N, 5.51.

What is claimed is:

1. A method of treating a subject suffering from a condition requiring SSR inhibition selected from the group consisting of post-traumatic stress disorder, premenstrual dysphoric disorder, attention deficit disorder, obesity, eating disorders, vasomotor flushing, cocaine and alcohol addiction, and sexual dysfunction which comprises providing to the subject suffering from said condition, a SSR inhibitory effective amount of a compound of formula I

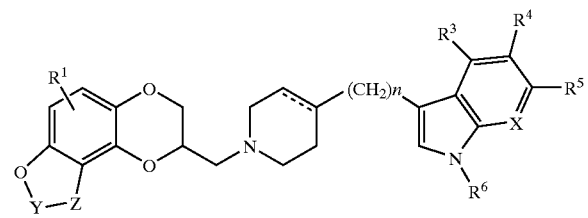

wherein $R^1, R^3, R^4, R^5$ and $R^7$ are, independently, hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

Y is C=O or $C(R^2)_2$ and Z is $CH_2$, $CH_2CH_2$, CH=CH or $NR_2$, or Y and Z, taken together, form $CR_2$=CH, N=$CR_2$ or $CR_2$=N;

$R^2$ and $R^6$ are hydrogen or alkyl of 1 to 6 carbon atoms;

X is $CR_7$ or N;

A dotted line represents an optional double bond; and n is an integer 0, 1 or 2; or a pharmaceutically acceptable salt thereof.

2. The method of claim 1 wherein the subject is a human.

* * * * *